US009662355B2

(12) United States Patent
Koob et al.

(10) Patent No.: US 9,662,355 B2
(45) **Date of Patent: *May 30, 2017**

(54) METHODS FOR TREATING CARDIAC CONDITIONS

(71) Applicant: MiMedx Group, Inc., Marietta, GA (US)

(72) Inventors: Thomas J. Koob, Marietta, GA (US); Frank H. Burrows, III, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/366,618

(22) PCT Filed: Jan. 17, 2014

(86) PCT No.: PCT/US2014/012141

§ 371 (c)(1),
(2) Date: Jun. 18, 2014

(87) PCT Pub. No.: WO2014/113733

PCT Pub. Date: Jul. 24, 2014

(65) Prior Publication Data

US 2015/0238540 A1 Aug. 27, 2015

Related U.S. Application Data

(60) Provisional application No. 61/849,838, filed on Jan. 18, 2013.

(51) Int. Cl.

| | |
|---|---|
| ***A61K 35/50*** | (2015.01) |
| ***A61K 38/17*** | (2006.01) |
| ***A61K 38/18*** | (2006.01) |
| ***C12N 5/073*** | (2010.01) |
| ***A61K 38/20*** | (2006.01) |
| ***A61K 38/57*** | (2006.01) |
| ***A61K 38/45*** | (2006.01) |

(52) U.S. Cl.

CPC .......... *A61K 35/50* (2013.01); *A61K 38/1709* (2013.01); *A61K 38/18* (2013.01); *A61K 38/1808* (2013.01); *A61K 38/1825* (2013.01); *A61K 38/1841* (2013.01); *A61K 38/1858* (2013.01); *A61K 38/1866* (2013.01); *A61K 38/2026* (2013.01); *A61K 38/2066* (2013.01); *A61K 38/45* (2013.01); *A61K 38/57* (2013.01); *C12N 5/0605* (2013.01); *C12Y 207/08001* (2013.01)

(58) Field of Classification Search

CPC .... A61K 35/50; A61K 38/1709; A61K 38/45; A61K 38/2026; A61K 38/1866; A61K 38/1858; A61K 38/57; A61K 38/2066; A61K 338/1808; A61K 38/18; A61K 38/1841

See application file for complete search history.

(56) References Cited

U.S. PATENT DOCUMENTS

| | | | |
|---|---|---|---|
| 2,694,914 | A | 11/1954 | Glover, Jr |
| 3,272,204 | A | 9/1966 | Artandi |
| 3,885,320 | A | 5/1975 | Hodson et al. |
| 4,703,108 | A | 10/1987 | Silver et al. |
| 4,807,442 | A | 2/1989 | Linner et al. |
| 4,847,049 | A | 7/1989 | Yamamoto |
| 4,865,871 | A | 9/1989 | Livesey et al. |
| 4,964,280 | A | 10/1990 | Piunno et al. |
| 5,118,867 | A | 6/1992 | Bahrmann et al. |
| 5,284,655 | A | 2/1994 | Bogdansky et al. |
| 5,541,232 | A | 7/1996 | Howell et al. |
| 5,780,295 | A | 7/1998 | Livesey et al. |
| 5,807,581 | A | 9/1998 | Rosenblatt et al. |
| 6,030,635 | A | 2/2000 | Gertzman et al. |
| 6,163,979 | A | 12/2000 | Oetjen et al. |
| 6,387,369 | B1 | 5/2002 | Pittenger et al. |
| 6,565,960 | B2 | 5/2003 | Koob et al. |
| 6,652,583 | B2 | 11/2003 | Hopkins et al. |
| 6,716,895 | B1 | 4/2004 | Terry |
| 6,936,271 | B1 | 8/2005 | Oliver et al. |
| 7,101,857 | B2 | 9/2006 | Sung et al. |
| 7,311,904 | B2 | 12/2007 | Hariri |
| 7,311,905 | B2 | 12/2007 | Hariri |
| 7,901,455 | B2 | 3/2011 | Koob et al. |
| 8,067,044 | B2 | 11/2011 | Henry et al. |
| 8,153,162 | B2 | 4/2012 | Tseng et al. |
| 8,177,839 | B2 | 5/2012 | Koob et al. |
| 8,192,481 | B2 | 6/2012 | King |
| 8,196,416 | B2 | 6/2012 | Uri et al. |

(Continued)

FOREIGN PATENT DOCUMENTS

| | | |
|---|---|---|
| CN | 101433556 | 5/2009 |
| EP | 0 431 164 A1 | 6/1991 |

(Continued)

OTHER PUBLICATIONS

EPIFIX brochure (2009); author unknown.*

Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.

Bauer S.M., et al., "Angiogenesis, vasculogenesis, and induction of healing in chronic wounds." Vascular and Endovascular Surgery, 2005, 39:293-306.

(Continued)

*Primary Examiner* — Daniel C Gamett

(74) *Attorney, Agent, or Firm* — Alston & Bird LLP

(57) ABSTRACT

Described herein are compositions and methods of treating a cardiac condition using modified placental tissue or an extract of a placental tissue, capable of recruiting stem cells or promoting healing in vivo and in vitro.

16 Claims, 8 Drawing Sheets

(56) References Cited

U.S. PATENT DOCUMENTS

| | | | |
|---|---|---|---|
| 8,409,626 B2 | 4/2013 | Daniel et al. | |
| 8,946,163 B2 | 2/2015 | Koob | |
| 8,961,617 B2 | 2/2015 | Young | |
| 2002/0160510 A1 | 10/2002 | Hariri | |
| 2003/0032179 A1 | 2/2003 | Hariri | |
| 2003/0143207 A1 | 7/2003 | Livesey et al. | |
| 2003/0187515 A1 | 10/2003 | Hariri et al. | |
| 2004/0028711 A1 | 2/2004 | Uchida et al. | |
| 2004/0048796 A1 | 3/2004 | Hariri et al. | |
| 2006/0140913 A1 | 6/2006 | Bhatia | |
| 2006/0210532 A1 | 9/2006 | Carmeliet et al. | |
| 2007/0020225 A1 | 1/2007 | Abramson et al. | |
| 2007/0071740 A1 | 3/2007 | Tseng et al. | |
| 2007/0071828 A1 | 3/2007 | Tseng et al. | |
| 2007/0144062 A1 | 6/2007 | Wright | |
| 2007/0202189 A1 | 8/2007 | Ahlfors | |
| 2007/0248575 A1 | 10/2007 | Connor et al. | |
| 2008/0050347 A1 | 2/2008 | Ichim | |
| 2008/0131966 A1 | 6/2008 | Hariri | |
| 2008/0193554 A1 | 8/2008 | Dua et al. | |
| 2008/0233552 A1 | 9/2008 | Ma et al. | |
| 2009/0012629 A1 | 1/2009 | Yao et al. | |
| 2009/0036996 A1 | 2/2009 | Roeber | |
| 2009/0053290 A1 | 2/2009 | Sand et al. | |
| 2009/0056162 A1 | 3/2009 | McMahon et al. | |
| 2009/0092664 A1 | 4/2009 | Mumper et al. | |
| 2009/0142831 A1 | 6/2009 | Hariri | |
| 2009/0287308 A1 | 11/2009 | Davis et al. | |
| 2009/0291891 A1 | 11/2009 | Neufeld | |
| 2010/0028849 A1 | 2/2010 | Shelby et al. | |
| 2010/0104539 A1 | 4/2010 | Daniel et al. | |
| 2010/0136114 A1 | 6/2010 | Mao | |
| 2010/0143312 A1 | 6/2010 | Hariri et al. | |
| 2010/0166716 A1 | 7/2010 | Serikov et al. | |
| 2010/0178297 A1 | 7/2010 | Carmeliet et al. | |
| 2010/0199514 A1 | 8/2010 | Camisa | |
| 2010/0209403 A1 | 8/2010 | Meiron et al. | |
| 2010/0209408 A1 | 8/2010 | Stephen et al. | |
| 2010/0260847 A1 | 10/2010 | Hariri | |
| 2010/0317677 A1 | 12/2010 | Hassel et al. | |
| 2011/0044997 A1 | 2/2011 | Rankin et al. | |
| 2011/0189301 A1 | 8/2011 | Yang et al. | |
| 2011/0206776 A1 | 8/2011 | Tom et al. | |
| 2011/0223142 A1 | 9/2011 | Sanford et al. | |
| 2011/0280834 A1 | 11/2011 | Forrester et al. | |
| 2011/0282448 A1 | 11/2011 | Paulos et al. | |
| 2011/0307059 A1 | 12/2011 | Young et al. | |
| 2012/0010708 A1 | 1/2012 | Young et al. | |
| 2012/0078378 A1 | 3/2012 | Daniel et al. | |
| 2012/0135045 A1 | 5/2012 | Nixon et al. | |
| 2012/0189571 A1 | 7/2012 | Sengupta et al. | |
| 2012/0189586 A1 | 7/2012 | Harrell | |
| 2012/0282348 A1 | 11/2012 | Yates et al. | |
| 2012/0294910 A1 | 11/2012 | Daniel et al. | |
| 2013/0095060 A1 | 4/2013 | Hsieh et al. | |
| 2013/0218274 A1 | 8/2013 | Spencer et al. | |
| 2013/0230561 A1 | 9/2013 | Daniel et al. | |
| 2013/0273008 A1 | 10/2013 | Lemper et al. | |
| 2014/0051059 A1 | 2/2014 | Pringle et al. | |
| 2014/0106447 A1 | 4/2014 | Brown et al. | |
| 2014/0140964 A1 | 5/2014 | Brown et al. | |
| 2014/0142025 A1 | 5/2014 | Koob | |
| 2014/0142041 A1 | 5/2014 | Koob | |
| 2014/0152648 A1 | 6/2014 | Sandrew et al. | |
| 2014/0186461 A1* | 7/2014 | Broussard | A61K 35/50 424/582 |
| 2014/0205646 A1 | 7/2014 | Morse et al. | |
| 2014/0242183 A1 | 8/2014 | Matheny | |
| 2014/0271728 A1 | 9/2014 | Koob et al. | |
| 2014/0308233 A1 | 10/2014 | Koob | |
| 2014/0356451 A1 | 12/2014 | Koob | |

FOREIGN PATENT DOCUMENTS

| | | | |
|---|---|---|---|
| EP | 0 431 479 | A1 | 6/1991 |
| EP | 0 506 207 | B1 | 11/1999 |
| KR | 2001/100588 | | 11/2001 |
| WO | WO-87/00062 | A1 | 1/1987 |
| WO | WO-88/03805 | A1 | 6/1988 |
| WO | WO-01/00151 | A1 | 1/2001 |
| WO | WO-2004/026244 | A2 | 4/2004 |
| WO | WO-2007/076522 | | 7/2007 |
| WO | WO-2007/083984 | A1 | 7/2007 |
| WO | WO 2009044408 | A1 * | 4/2009 |
| WO | WO-2011/103470 | | 8/2011 |
| WO | WO-2011/127117 | | 10/2011 |
| WO | WO-2012/003377 | | 1/2012 |
| WO | WO-2012/065937 | A1 | 5/2012 |
| WO | WO-2012/069559 | A1 | 5/2012 |
| WO | WO-2012/112417 | A2 | 8/2012 |
| WO | WO 2012112410 | A2 * | 8/2012 |

OTHER PUBLICATIONS

Bennett JP, et al., "Treatment of chronic ulceration of the legs with human amnion" Lancet, 1980, 1:1153-1156.

Blakytny R.,"The molecular biology of chronic wounds and delayed healing in diabetes", Diabetic medicine A journal of the British Diabetic Association. 2006, 23:594-608.

Borkow et al., "Reducing the risk of skin pathologies in diabetics by using copper impregnated socks", Medical Hypotheses, 2009, 1-4, doi:10.1016/j.mehy.2009.02.050.

Carmeliet et al., "Synergism between vascular endothelial growth factor and placental growth factor contributes to angiogenesis and plasma extravasation in pathological conditions." Nature Medicine, 2001, 7:575-583.

Database WPI XP002732611 & KR 2001-0100588, dated Nov. 14, 2001-Abstract.

Derwent Abstract for KR 200110588, original document published Nov. 2001.

Dua et al., "The amniotic membrane in ophthalmology", Survey of Ophthalmology, 2004, 49:51-77.

Ennis et al. "Clinical experience with a novel regenerative template for hard to heal wounds." In SAWC Annual Spring Meeting; Atlanta, GA. 2012.

EpiFix Product Brochure (2011).

Extended European Search Report dated Dec. 2, 2014, for European Patent Application No. EP 12746721.

Faulk et al. "Human amnion as an adjunct in wound healing." Lancet, 1980, 1:1156-1158.

Forbes et al., "Dehydrated amniotic membrane allografts for the treatment of chronic wounds: a case series." Journal of Wound Care, 2012, 21:290, 292, 294-296.

Gruss et al. "Human amniotic membrane: a versatile wound dressing." Canadian Medical Association Journal, 1978, 118:1237-1246.

Hannallah et al., "Cerebrospinal fluid leaks following cervical spine surgery," J. Bone Joint Surg. Am., (2008), 90(5):1101-1105.

Hao et al., "Identification of antiangiogenic and antiinflammatory proteins in human amniotic membrane." Cornea, 2000, 19:348-352.

Hattori et al., "Placental growth factor reconstitutes hematopoiesis by recruiting VEGFR1+ stem cells from bone-marrow microenvironment," Nat. Med., (2002), 8(8):841-849.

http://proxbiomedical.com/Images/ML005-01-Rev002.pdf (accessed on Jun. 5, 2014.).

Inokuma et al., "CTACK/CCL27 Accelerates Skin Regeneration via Accumulation of Bone Marrow-Derived Keratinocytes", Stem Cells, 2006, 24:2810-2816.

International Preliminary Report on Patentability for PCT Application No. PCT/US2014/012141 dated May 14, 2015.

John, T., "Human amniotic membrane transplantation: past, present, and future" Ophthalmology Clinics of North America, 2003, 16:43-65, vi.

Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.

(56) References Cited

OTHER PUBLICATIONS

Kim et al., "The effects on inhibition of corneal neovascularization after human amniotic membrane transplantation in severely damaged rabbit corneas", Korean Journal of ophthalmology, 1995, 9:32-46.
Kim K.A., et al., "Dysfunction of endothelial progenitor cells under diabetic conditions and its underlying mechanisms", Archives of Pharmacal Research, 2012, 35:223-234.
Koizumi., et al., "Growth factor mRNA and protein in preserved human amniotic membrane", Current Eye Research, 2000, 20:173-177.
Koob et al., "Biological properties of dehydrated human amnion/chorion composite graft: implications for chronic wound healing," International Wound Journal, (2013), 10(5):493-500.
Kubo et al., "Immunogenicity of human amniotic membrane in experimental xenotransplantation", Investigative ophthalmology & Visual Science, 2001, 42:1539-1546.
Li et al., "Angiogenesis in wound repair: angiogenic growth factors and the extracellular matrix." Microscopy Research and Technique, 2003, 60:107-114.
Lopez-Valladares et al., "Donor age and gestational age influence on growth factor levels in human amniotic membrane", Acta Ophthalmologica, 2010, 88:e211-216.
Lu et al., "Molecular mechanisms and clinical applications of nordihydroguaiaretic acid (NDGA) and its derivatives: An update," Med. Sci. Monit., (2010), 16(5):RA93-RA100.
Mayfield et al., "Watertight closure of spinal dura mater: Technical note," J. Neurosurg., (1975), 43(5):639-640.
Mermet et al., "Use of amniotic membrane transplantation in the treatment of venous leg ulcers. Wound repair and regeneration", official Publication of the Wound Healing Society [and] the European Tissue Repair Society, 2007, 15:459-464.
MiMedx Group Announces Launch of EpiFixTM and Hiring of Vice President, Wound Care, Mimedx Press Release (2011).
MiMedx Press Release, "MiMedx Scientific Study is Electronically Published in the International Wound Journal", 2013.
Moussy et al., "Transport characteristics of a novel local drug delivery system using nordihydroguaiaretic acid (NDGA)-polymerized collagen fibers", Biotechnology Progress, Aug. 31, 2007, vol. 23, No. 4, pp. 990-994.
MyBioSource/www.mybiosource.com/prods/Recombinant-Protein/CCL27-CTACK/datasheet.php?products-id-444088> Accessed Jun. 9, 2015).
Nagaya et al., "Transplantation of mesenchymal stem cells improves cardiac function in a rat model of dilated cardiomyopathy", Circulation, 2005, 112(8):1128-1135.
Nibbs et al., "CCL27/Pesky: A Novel Paradigm for Chemokine Function", 2003, Expert Opin. Biol. Ther., 3(1):15-22.
Parolini et al., 'Toward cell therapy using placenta-derived cells: disease mechanisms, cell biology, preclinical studies, and regulatory aspects at the round table', Stem Cells and Development, 2010, vol. 19, No. 2, pp. 143-154.
Patent Examination Report for AU Patent Application No. 2012217975 dated May 8, 2015.
PCT International Search Report and Written Opinion for PCT Patent Application No. PCT/US2014/012141 dated May 20, 2014. 13 pages.
Rennert et al. "Stem Cell Recruitment after Injury: Lessons for Regenerative Medicine", Regen Med., Nov. 2012, 7(6): 833-850.
Russo et al., "The effects of different preservation processes on the total protein and growth factor content in a new biological product developed from human amniotic membrane." Cell and Tissue Banking, 2012, 13:353-361.
Serena et al., "Clinical Research: Dehydrated human amniotic membrane dHAM) treatment of lower extremity venous ulceration (CR23)." In SAWC Annual Spring Meeting; Atlanta, GA. 2012.
Sheikh et al., "Use of dehydrated human amniotic membrane allografts to promote healing in patients with refractory non healing wounds", International Wound Journal, 2014, 11:711-717.
Smiell et al., "Efficacy and safety of becaplermin (recombinant human platelet-derived growth factor-BB) in patients with nonhealing, lower extremity diabetic ulcers: a combined analysis of four randomized studies", Wound Repair and Regeneration, Official Publication of the Wound Healing Society [and] the European Tissue Repair Society, 1999, 7:335-346.
Steed et al." Amnion-derived cellular cytokine solution: a physiological combination of cytokines for wound healing", Eplasty, 2008, 8:e18.
Subrahmanyam, M., "Amniotic membrane as a cover for microskin grafts", British Journal of Plastic Surgery, 1995, 48:477-478.
Toda et al., "The potential of amniotic membrane/amnion-derived cells for regeneration of various tissues." Journal of Pharmacological Sciences, 2007, 105:215-228.
Tonnesen et al., "Angiogenesis in wound healing", The Journal of Investigative Dermatology Symposium Proceedings / the Society for Investigative Dermatology, Inc. [and] European Society for Dermatological Research, 2000, 5:40-46.
Uberti et al., "Amnion-derived cellular cytokine solution (ACCS) promotes migration of keratinocytes and fibroblasts", Annals of Plastic Surgery, 2010, 64:632-635.
Ueta, M., "Immunosuppressive properties of human amniotic membrane for mixed lymphocyte reaction", Clinical and Experimental Immunology, 2002, 129:464-470.
Ventura et al. Hyaluronan Mixed Esters of Butyric and Retinoic Acid Drive Cardiac and Endothelial Fate in Term in Term Placenta Human Mesenchymal Stem Cells and Enhance Cardiac Repair in Infarcted Rat Hearts, The Journal of Biological Chemistry, 282 (2007) 14243-14254.
Waterman et al. A New Mesenchymal Stem Cell (MSC) Paradign: Polarization Into a Pro-Inflammatory MSC1 or an Immunosuppressive MSC2 Phenotype, PLos One 5(4); Apr. 2010, pp. 1-14.
Werner et al. "Regulation of wound healing by growth factors and cytokines", Physiological Reviews, 2003, 83:835-870.
Wieman et al., "Efficacy and safety of a topical gel formulation of recombinant human platelet-derived growth factor-BB (becaplermin) in patients with chronic neuropathic diabetic ulcers. A phase III randomized placebo-controlled double-blind study", Diabetes Care, 1998, 21:822-827.
Zaja-Milatovic et al., "CXC Chemokines and Their Receptors: A case for a significant Biological Role in Cutaneous Wound Healing, Histol", Histopathol., Nov. 2008, 23(11):1399-1407.
Zelen et al. "A prospective randomised comparative parallel study of amniotic membrane wound graft in the management of diabetic foot ulcers", International Wound Journal, 2013, 10:502-507.

* cited by examiner

METHODS FOR TREATING CARDIAC CONDITIONS

CROSS-REFERENCE TO RELATED APPLICATION

This application is a national stage application under 35 U.S.C. §371 of International Application No. PCT/US2014/012141, filed Jan. 17, 2014, which claims the benefit under 35 U.S.C. §119(e) of U.S. Provisional Patent Application No. 61/849,838, filed on Jan. 18, 2013, all of which are hereby incorporated by reference in their entirety.

BACKGROUND

Field of the Invention

This invention is directed, in part, to methods of treating cardiac conditions by use of a sufficient amount of modified placental tissue or an extract of a placental tissue.

State of the Art

Despite advances in patient care and treatment, cardiovascular diseases remain the biggest cause of deaths worldwide.

There are about 6 million Americans living with heart failure (HF), and there are 670,000 new cases of HF each year. HF is the primary reason for 12-15 million office visits and 6.5 million hospital days annually. The economic burden and overall healthcare impact of HF are staggering. Indeed, it is estimated that the total direct and indirect costs for HF in the United States exceed $30 billion each year. Remarkably, atherosclerotic coronary artery disease (CAD) accounts for 60-75% of all symptomatic HF, with the history of MI conferring an increased relative risk of 6.0 for HF.

Therefore, there is need for additional treatment options for cardiovascular diseases, such as heart failure.

SUMMARY OF THE INVENTION

Cardiac conditions by and large involve damaged cardiac tissue such as damage cardiac muscles arising from ischemic events, damages to the left ventricle such as those arising from congested heart failure, damages to the heart valves arising from diseases, such as coronary artery diseases. In all aspects, improving function of the damaged portion of the cardiac tissues would be a benefit to the patient. Conventional treatments include introducing a mechanical device, such as a stent, an external pump, and the like, to treat the disease or the condition. Other treatment conditions include coronary bypass procedures where the coronary arterial blockage is circumvented by introduction of an autologous vessel such as a leg vein which is connected to the artery by anastomosis.

This invention is directed to the discovery that modified placenta tissue, possesses numerous biological factors that induce the patient's healing of the damaged organ or tissue. Such factors include stem cell recruiting factors, growth factors and angiogenesis inducing factors, all of which either alone or in combination, interact to minimize damage and to heal already damaged cardiac tissue.

Accordingly, in one aspect, there is provided a method for treating a cardiac condition in a patient in need thereof, comprising administering to said patient a sufficient amount of a composition comprising a modified placental tissue or an extract of a placental tissue.

In one aspect, provided is a composition comprising modified placental tissue configured for non-obstructive placement to an area approximate to a damaged cardiac tissue in an amount sufficient to minimize damage and induce healing. For example, the placenta tissue may be introduced at or approximate to the damage, to induce healing of the tissue, by biological processes including angiogenesis. In some embodiments, the modified placental tissue retains an effective amount of stem cell recruiting factors, growth factors, and/or angiogenesis inducing factors.

In another aspect, provided is a method for treating damaged or diseased cardiac tissue, which method comprises placing an effective amount of a modified placental tissue or an extract of a placental tissue approximate to the damaged cardiac tissue without obstructing the function thereof, wherein the modified placental tissue or the extract is placed under conditions that promote treatment of the disease or healing of the damaged tissue.

In another aspect, provided is a method for treating a cardiac condition in a patient in need thereof comprising providing to an area proximate to the heart of the patient with a composition comprising a modified placental tissue or an extract of a placental tissue comprising an effective amount of stem cell recruiting factors, wherein said modified placental tissue or extract, when placed in contact with said area, promotes stem cell recruitment to said area. In one embodiment, the stem cell recruited is a hematopoietic stem cell (HSC). In another embodiment, the stem cell recruited is a mesenchymal stem cell (MSC). In one embodiment, the stem cell recruited is bone marrow-derived stem cells.

These and other aspects of this invention are further described herein.

BRIEF DESCRIPTION OF THE DRAWINGS

The accompanying drawings, which are incorporated in and constitute a part of this specification, illustrate several aspects described below.

FIG. 4A shows quantitation of infarct size relative to total area of the heart from membrane treated mice and control treated mice is shown. Three sections were taken of each heart and quantitation of infarct size was performed on the two sections proximal to the site of infarct. The sections were stained with Masson's trichrome. FIG. 4B shows representative images of membrane treated and control treated wild-type and NOD/SCID mice. AmnioFix® membrane=membrane 2, 3, 4 and 6; EpiFix® membrane=membrane 1, 5 and 7. *$p<0.05$, **$p<0.001$. Details are described in Example 6.

FIG. 5A shows schematic depiction of the placement of the AmnioFix® or EpiFix® membrane. FIG. 5B shows representative immunohistochemical staining for c-kit for regions of the heart covered by the AmnioFix® or EpiFix® membrane or regions peripheral to the membrane. FIG. 5C shows quantitation of c-kit+ cells in the tissue sections. Details are described in Example 6.

FIG. 6A shows representative immunocytochemical staining of membrane and control-treated hearts. The treated hearts were stained for Ki-67 (green) and the cardiac muscle cell marker troponin, Troponin C(red). DAPI is in blue. FIG. 6B shows quantitation of the Ki-67+ cells from the membrane treated compared to control treated hearts. Details are described in Example 6.

FIG. 7A shows CD31 staining (green) of the membrane treated and control treated hearts indicated a significant increase in the number of blood vessels. The sections were co-stained for troponin (red) and DAPI (Blue). FIG. 7B shows quantitation of mean number of vessels in membrane (EpiFix® and AmnioFix®) treated hearts compared to saline treatment (control). Details are described in Example 6.

FIG. 8A shows TUNEL staining was used to identify apoptotic cells in the membrane and control-treated heart tissue. FIG. 8B shows quantitation of TUNEL positive cells in the membrane and control treated cells. Details are described in Example 6.

DETAILED DESCRIPTION

Definitions

Figure 1:
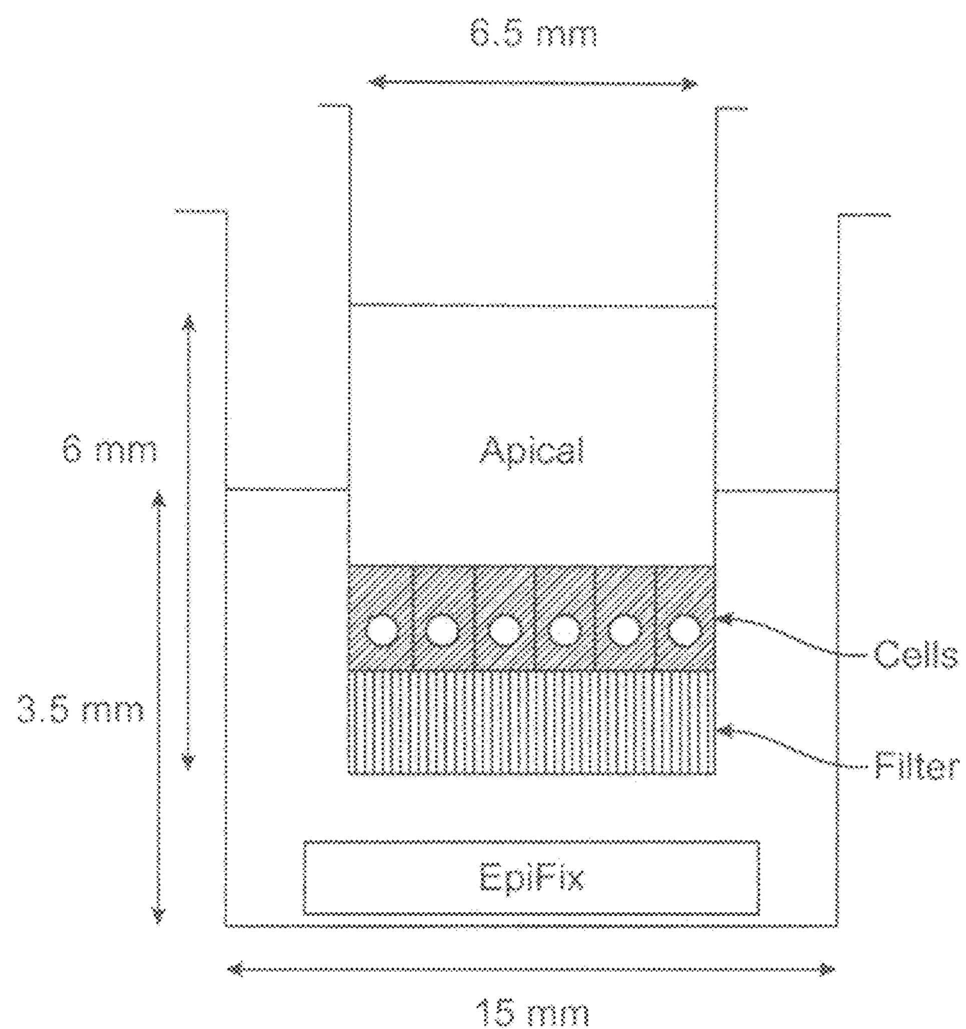
FIG. 1 shows a schematic for a cell culture insert for stem cell migration assays described in Example 3.

Before this invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" or "patient" as used herein refers to any vertebrate organism including, but not limited to, mammalian subjects such as humans, farm animals, domesticated pets and the like.

The term "amnion" as used herein includes amniotic membrane where the intermediate tissue layer is intact or has been substantially removed.

The term "exterior surface" refers to either or both surfaces of the modified placental tissue which will contact the diseased or injured cardiac tissue of the patient to which the placental tissue is applied.

The term "cardiac tissue" as used herein refers to any part of the heart including the pericardium, the endocardium, the myocardium and the epicardium, as well as blood vessels and nerves on or connected to the heart, etc.

The term "diseased" as used herein refers to an organ and/or body part, such as a cardiac tissue, that is characterized as being in a disease state, or susceptible to being in a disease state.

The term "injured" as used herein is used to have an ordinary meaning in the art, and includes any and all types of damage to an organ and/or body part, such as a cardiac tissue.

The term "biocompatible" as used herein refers to a material that is suitable for implantation or injection into a subject. In various aspects, a biocompatible material does not cause toxic or injurious effects once implanted in the subject.

The term "modified placental tissue" refers to any and all components of placental tissue including whole placental tissue that has been modified by cleaning, disinfecting, and/or segmenting the tissue as well as to separated components of placental tissue such as amnion, chorion, the umbilical cord, and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "extract of a placental tissue" refers to a composition, such as a solution or a lyophilized solid, comprising one or more of the biological factors present in a placental tissue or modified placental tissue and substantially free of the placental tissue or cell materials.

The term "sufficient amount" or "effective amount" refers to an amount of a modified placental tissue or an extract of a placental tissue that is sufficient to inhibit, reduce or minimize a cardiac damage or induce healing of the diseased or injured cardiac tissue over time, either in vivo or in vitro. The "sufficient amount" will vary depending on a variety of factors, such as but not limited to, the type and/or amount of the placental tissue or extract of a placental tissue used, the type and/or size of the diseased or injured cardiac tissue to be treated, the severity of the disease or injury to the diseased or injured cardiac tissue to be treated and the administration route. The determination of a "sufficient amount" can be made by one of ordinary skill in the art based on the disclosure provided herein.

The term "placental growth factors" refers to that array of growth factors obtainable from modified placental tissue. The manner of obtaining such growth factors is not critical to the invention and include, by way of example only, aqueous extraction from the placenta, culturing of placental cells expressing such growth factors, and the like. The concentration of extracted growth factors can be increased by reducing the volume of water, saline, or buffer used to extract the growth factors, by addition of growth factors produced from placental cell cultures, and the like.

The term "stem cell recruiting factors" refers to any and all factors that are capable of inducing the recruitment of stem cells and causing them to migrate towards a source of such factors. Non-limiting examples of stem cell recruiting factors may be one or more CC chemokines, CXC chemokines, C chemokines, or $CX_3C$ chemokines.

The term "stem cell recruitment" refers to direct or indirect chemotaxis of stem cells to a modified placental tissue or an extract of a placental tissue. In one aspect, the recruitment may be direct, wherein stem cell recruiting factors (e.g. chemokines, which induce cell chemotaxis) in a modified placental tissue are released from the placental tissue or extract comprising such factors are introduced to the site to be treated and which induce stem cells to migrate towards the site. In another aspect, the recruitment may be indirect, wherein stem cell recruiting factors alone or in a modified placental tissue induce nearby cells to release factors (e.g. chemokines), that in turn induce stem cells to migrate towards the placental tissue. Still further, stem cell recruitment may embody both direct and indirect factors.

The term "proximate to" as used herein means adjacent to, or contacting a body part, such as a diseased or injured cardiac tissue, such that the composition exerts the desired effect. In general, "proximate to" means a distance that is generally within the skill of the art but preferably is within 3 cm, 2 cm, or 1 cm of the organ or body part, including on or in the body part. The term "contact" or "contacting" means that the composition is on or in the body part.

The term "exogenous" refers to substances that are not naturally occurring to a body part being treated, including allograft tissue, such as modified placental tissue.

The term "endogenous" refers to autologous biological substances from a subject.

As used herein, the term "bioerodible," which is used herein interchangeably with the term "biodegradable," refers to a biocompatible material that gradually decomposes, dissolves, hydrolyzes and/or erodes in situ, or that is susceptible to degradation into smaller components or molecules in a living organism over a prolonged period of time, for example, over days or months, such that the material is harmless to the living organism under normal living conditions. Generally, the "bioerodible" polymers herein are polymers that are hydrolyzable, and bioerode in situ primarily through hydrolysis. Preferably, the smaller components or molecules are biocompatible to a patient.

As one of ordinary skill in the art would understand, the degradation of the material results in a continuous release of a therapeutic amount of placental growth factors incorporated in the material over a prolonged period of time, such as about 3 days, about 5 days, about 10 days, about 15 days, about 20 days, about 25 days, about 30 days, about 2 months, about 3 months, about 4 months, about 5 months, or about 6 months. A desired release rate can be determined and/or achieved by adjusting the initial concentration of the growth factors incorporated in the bioerodible or biodegradable mass and the degradation rate of the mass.

Titles or subtitles may be used in the specification for the convenience of a reader, which are not intended to influence the scope of the present invention. Additionally, some terms used in this specification are more specifically defined below.

Compositions and Methods

When a heart tissue, such as heart muscle, is damaged, for example, in a heart attack, stem cells can be recruited to make repairs. However, it is believed that the heart has a tendency to stop signaling for stem cells before the repair is complete. As a result, the damaged tissue may be only partially repaired, which becomes a burden to the heart, forcing it to work harder and less efficiently, and possibly leading to additional harmful effect to the heart. Further, current therapeutic injections of stem cells into the damaged tissue are complicated by the low rate of survival of injected stem cells.

This invention is based, in part, on the discovery that application of a sufficient amount of a composition comprising a modified placental tissue, such as amnion, or an extract of a placental tissue, proximate to a diseased or injured cardiac tissue of a patient not only provides an exogenous treatment regimen but surprisingly also provides an endogenous therapeutic effect through eliciting, directly or indirectly, stem cell recruitment to the site of the diseased or injured body part, thereby achieving a binary therapeutic effect. In the case of placental tissue, it is contemplated that administration of the modified placental tissue to the diseased or injured cardiac tissue not only provides a physical remedy and/or barrier to prevent undesired tissue adhesion but also induces an endogenous effect by improving the efficiency of stem cell recruitment and/or recruits stem cell when the heart itself fails to do so. It is further contemplated that the modified placental tissue or extract stimulates growth and healing of the diseased or injured tissue by providing growth factors and/or angiogenesis inducing factors to the diseased or injured tissue, separately or in combination with inducing stem cell recruitment.

Accordingly, in one aspect, provided is a composition comprising a placental tissue or factors extracted from a placental tissue which is delivered for the non-obstructive placement to an area approximate to a diseased or injured cardiac tissue in an amount sufficient to reduce damage and induce healing. In some embodiments, the modified placental tissue or an extract of a placental tissue comprises an effective amount of stem cell recruiting factors, growth factors, and/or angiogenesis inducing factors. In some embodiments, the placenta tissue or an extract of a placental tissue induces healing of the tissue by biological processes including angiogenesis.

In another aspect, there is provided a method for treating a cardiac condition in a patient in need thereof, comprising administering to said patient an sufficient amount of a composition comprising a modified placental tissue or an extract of a placental tissue. In some embodiments, the composition is administered by being placed approximate to a cardiac tissue having or causing the cardiac condition.

In another aspect, provided is a method for treating diseased or injured cardiac tissue, which method comprises placing an effective amount of a modified placental tissue or an extract of a placental tissue configured to being placed approximate to the diseased or injured heart tissue without obstructing the function thereof, wherein the modified placental tissue or extract of a placental tissue is placed under conditions that promote treatment of the disease or healing of the injured tissue.

In another aspect, provided is a method for treating a cardiac condition in a patient in need thereof comprising providing to an area proximate to the heart of the patient with a composition comprising a modified placental tissue or an extract of a placental tissue which comprises an effective amount of stem cell recruiting factors, growth factors and angiogenesis inducing factors, wherein said modified placental tissue or extract, when placed in contact with or proximate to said area, promotes stem cell recruitment to said area and/or healing of the cardiac tissue. In one embodiment, the stem cell recruited is a haematopoietic stem cell (HSC). In another embodiment, the stem cell recruited is a mesenchymal stem cell (MSC). In another embodiment, the stem cell recruited is bone marrow derived stem cell.

In another aspect, provided is a method for treating a cardiac condition comprising a diseased or injured cardiac tissue in a patient in need thereof, comprising contacting said cardiac tissue with a sufficient amount of a composition comprising a modified placental tissue or an extract of a placental tissue which comprises an effective amount of stem cells recruiting factors, growth factors and angiogenesis inducing factors.

In some embodiments, the cardiac condition is selected from an inflammatory heart condition, such as myocarditis, pericarditis and endocarditis, and a necrotizing condition.

In some embodiments, the cardiac condition is selected from acute myocardial infarction, myocardial infarction, cardiomyopathy (e.g., ischemic cardiomyopathy, myocarditis or inflammatory cardiomyopathy, dilated cardiomyopathy, and hypertrophic cardiomyopathy), unstable angina, refractory angina, heart attack, heart failure, cor pulmonale, vein graft diseases such as degeneration and occlusion of saphenous vein grafts, coronary heart diseases, occlusive coronary thrombus (e.g., thrombus occurring post-thrombolytic therapy or post-coronary angioplasty). In some embodiments, the cardiac condition is inflammation of a heart valve. In some embodiments, the cardiac condition is selected from valvular heart disease, inflammatory cardiomegaly, and atherosclerosis.

Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The modified placental tissue can be used as a patch to support the repair of vascular and cardiac defects caused by operations and complications such as carotid artery repair, coronary artery bypass grafting, congenital heart disease, heart valve repair, and vascular repair (i.e. peripheral vessels).

In some embodiments, the method is for promoting healing of a surgical site of the heart and/or reducing scarring. In some embodiments, the method is for promoting tissue regrowth after a cardiac surgery, such as a valve repair or anastomosis.

In some embodiments, the method is for treating a pericardial disease, such as acute pericarditis. In some embodiments, the method is used during and/or after replacement of pericardium. In some embodiments, the method is for treating Dresslers syndrome or reducing inflammation in Dresslers syndrome.

In some embodiments, the placental tissue attracts endogenous stem cells and provide a microenvironment for stem cell survival.

In some embodiments, the placental tissue is preconditioned in vitro, so as to facilitate the proliferation and optional differentiation of the exogenous stem cells into cardiomyogenic lineage.

In some embodiments, the placental tissue is a biocompatible and nontoxic support material for the stem cells.

In some embodiments, the placental tissue material is a patch, and represents a structurally resistant element that serves as a bandage for the diseased or injured area. More specifically, the placental tissue material functions as a molecular and mechanical bandage, serving as chemoattractant for endogenous stem cells (e.g., cardiac and/or bone marrow) to migrate to the site of injury and stimulating their proliferation to promote healing, therefore, reduce scar tissue formation and inhibiting inflammation.

In some embodiments, the placental tissue material is integrated within the host tissue and optionally replaced by the host extracellular matrix (ECM).

In one embodiment, placental tissue may be modified as described in U.S. Ser. No. 61/683,698, including cleaning, separation of the amnion and chorion, removal or maintenance of the epithelial cell layer, decontamination, and dehydration. Dehydration may be accomplished using the drying apparatus or chemical dehydration, for example, as described in U.S. Ser. No. 13/691,509, filed Nov. 30, 2012. Both of which applications are incorporated herein by reference in their entirety. Each aspect of that process produces modified placental tissue for the purposes of this invention whether used alone or in combination. However, it is preferred that the modified placental tissue include at least the steps of cleaning and decontamination. As such, modified placental tissue preferably comprises placental tissue which has been cleaned and decontaminated and also includes placental tissue which has undergone one or more of separation of the amnion and chorion, removal of the epithelial cell layer, and dehydration. Modified placental tissue can also be formed into layers which may be dried separately and laminated together or dried together to form multi-layer laminates.

Modified placental tissue may also be micronized into particles of a variety of sizes, for example, no more than about 300 microns in size, such as less than about 250 microns, less than about 200 microns, less than about 150 microns, less than about 100 microns, or less than about 50 microns. Micronized placental tissue may be sandwiched between one or more layers of a multilayer laminate, or on top of a laminate. Micronized placental tissue may also be added to single layer of modified placental tissue. See, for example, International Patent Application No. PCT/US2012/024798, filed Feb. 13, 2012, as well as U.S. Provisional Patent Application Ser. No. 61/683,700 filed Aug. 15, 2012 both of which are incorporated herein by reference in their entirety. It is also contemplated that micronized modified placental tissue can enhance the rate of stem cell recruitment in a particular body part. In some embodiments, micronized modified placental tissue is added to modified placental tissue, either a single layer of modified placental tissue, or in between a multi-layer laminate of placental tissue.

In some embodiments, the modified placental tissue is selected from amnion, chorion, or both amnion and chorion. In some embodiments, modified placental tissue does not include the umbilical cord.

Amnion is a unique ECM due to the presence of collagen types IV, V and VII, which enables the amnion to bind water and swell. The intermediate tissue layer of the amniotic membrane is composed largely of glycoproteins and proteoglycans, which also enables the intermediate tissue layer to bind water. Thus, the modified placental tissue when applied to a diseased or injured cardiac tissue helps retain water at that site, which facilitates cardiac tissue repair and/or regeneration. For example, cell migration, including stem cell recruitment, within the healing cascade is facilitated in a hydrophilic environment. The intermediate layer is also composed of collagen types I, III, and IV. Type I collagen provides mechanical strength to skin by providing a major biomechanical scaffold for cell attachment and anchorage of macromolecules. Type III collagen provides elasticity.

In other embodiments, the epithelial cell layer of the amnion is not removed. In these embodiments, the modified placental tissue provides additional protection by maintaining separation from the peritoneum, larger vessels, and abdominal musculature. The modified placental tissue may serve as a reduced friction anatomical barrier against adhesions and scaring. In one embodiment, the application of the modified placental tissue described herein where the epithelial layer of the skin is disrupted can be effective in delivering the growth factors directly to the injured site to promote healing and/or stem cell recruitment.

In some embodiments, the epithelium of the amnion is substantially removed. Removal of the epithelial cell layer exposes the amnion's basement membrane layer, which increases cell signaling characteristics. This up regulation response enhances cellular migration and expression of anti-inflammatory proteins, which inhibits fibrosis.

In some embodiments, the composition comprising a modified placental tissue or extract of a placental tissue is provided to an area adjacent to a diseased or injured cardiac tissue via injection of a composition comprising a micronized modified placental tissue or the extract, via surgical implantation of the composition or via patch delivery of the composition.

In some embodiments, the composition comprising a modified placental tissue or extract is in an injectable form comprising micronized modified placental tissue or extract and a pharmaceutically acceptable carrier. Suitable pharmaceutically acceptable carriers include, but are not limited to, such as water, a buffer (e.g., phosphate buffered saline (PBS), citrate buffer, etc.), water-soluble organic solvents (e.g., polyethylene glycol 300, polyethylene glycol 400, ethanol, propylene glycol, glycerin, N-methyl-2-pyrrolidone, dimethylacetamide, and dimethylsulfoxide), organic liquids/semi-solids (beeswax, d-tocopherol, oleic acid, medium-chain mono- and diglycerides), non-ionic surfactants (polyethoxylated castor oils (e.g., Cremophor EL, Cremophor RH 40, Cremophor RH 60), polysorbate 20, polysorbate 80, poloxamer 188, poloxamer 407, d-tocopherol polyethylene glycol 1000 succinate, polyethylene glycol (15)-hydroxystearate, sorbitan monooleate, oleoyl polyoxyl-6 glycerides, linoleoyl polyoxyl-6 glycerides, caprylocaproyl polyoxyl-8 glycerides, Gellucire® 44/14, Softigen® 767, and mono- and di-fatty acid esters of PEG 300, 400, or 1750, etc.), a lipid (e.g., castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil), cyclodextrin (such as α-cyclodextrin, β-cyclodextrin, and γ-cyclodextrin, hydroxypropyl-β-cyclodextrin, and sulfobutylether-β-cyclodextrin), and phospholipids (e.g., phosphatidylcholine, phosphatidylethanolamine, phosphatidylserine, distearoylphosphatidylglycerol, 1-dimyristoylphosphatidylcholine, 1-dimyristoylphosphatidylglycerol, etc.), or a mixture thereof.

In some embodiments, the composition forms a localized mass when applied to or proximate to said diseased and/or injured cardiac tissue with an agent which allows for localized retention of the solution or suspension at the site of delivery optionally for extended and/or continuous release of the biological factors in the composition. Such agents include thixotropic agents, phase changing agents, and the like. These compositions are in an injectable form at ambient conditions and form a viscous or gel-like bioerodible or biodegradable mass in vivo which limits transport away from the site of delivery and allows for the diffusion of the biological factors from the mass formed over a period of time.

In some embodiments, localization agents, such as thixotropic agents, phase changing agents, and the like, may include but not limited to, hydrogel, bioerodible, biocompatible polymer, and collagen gels. The presence of one or more localization agents in the compositions of this invention allows the compositions to have certain viscosity such that the compositions are locally retained for a period of time upon administration or injection. It is within the purview of one of ordinary skill in the art to determine the suitable viscosity of the compositions. In some aspects, the compositions have a viscosity between about 5 cP to about $1\times10^8$ cP, or about 5 cP to about $1\times10^6$ cP, or about 5 cP to about $1\times10^5$ cP, or about 5 cP to about $1\times10^4$ cP, or about 5 cP to about $1\times10^3$ cP, or about 6 cP to about 9500 cP at 25° C.

The hydrogels useful in the compositions of this invention can be chemically and/or physically cross-linked hydrogels. In situ chemical cross-linking is obtained, e.g., via photo-initiated, redox-initiated or Michael-type addition polymerization that preferably involve covalent bond formation. Physically cross-linked hydrogels self-assemble under external stimuli and do not rely on covalent bond formation. Temperature, pH, ion concentration, and hydrophobic interactions are certain of the external stimuli useful for such self-assembly and for the immobilization of such hydrogels.

Exemplary polymers suitable for the use in the composition of the present invention include polylactides, polyglycolides, poly(caprolactone), polyanhydrides, polyamines, polyesteramides, polyorthoesters, polydioxanones, polyacetals, polyketals, polycarbonates, polyphosphoesters, polyorthocarbonates, polyphosphazenes, succinates, poly(malic acid), poly(amino acids), polyvinylpyrrolidone, polyethylene glycol, polyhydroxycellulose, polyphosphoesters, polysaccharides, chitin, chitosan, hyaluronic acid, and copolymers, terpolymers and mixtures thereof.

Collagens can be used include, for example, alkaline treatment of insoluble collagen extracted from various animals, or by treating with enzyme such as pepsin, trypsin, chymotrypsin, papin or pronase. There are no particular restrictions on the origin of the collagen, and typically collagen can be used that is obtained from the skin, bone, cartilage, tendon or organs, etc. of birds or mammals, Since collagen allows the obtaining of a suitable consistency without heating, preparation can be made easily in the case of gelation. In addition, collagen has a high molecular weight, it more closely resembles living body tissue, has considerable physiological activity, and therefore promotes healing in the case of using on a wound, resulting in a further therapeutic effect in combination with the modified placental tissue. Collagen can be flexible after curing and requires only a short time for crosslinking, in other words, requires only a short time for gelation. Collagen solution can also be made by dissolving in a non-toxic solvent respect to the living body, examples of which include water, physiological saline, a buffer such as borate buffer, or an aqueous solution containing a salt such as sodium chloride, sodium bromide and potassium bromide, or protein, sugar or lipid, etc.

The collagen can also form a gel even in the presence of moisture such as that in blood or humor, and can demonstrate a high degree of adhesiveness with respect to living body tissue. Collagen solutions used in the present invention can be made at various concentrations, neutralized and prepared for injection. In various aspects, collagen at 0.2 mg/mL, 0.5 mg/mL, 0.75 mg/mL, 1 mg/mL, 2 mg/mL, 3 mg/mL, 4 mg/mL, 5 mg/mL, 6 mg/mL, 7 mg/mL, 8 mg/mL, 10 mg/mL, 20 mg/mL, 30 mg/mL, 40 mg/mL and 50 mg/mL in solution can be used for injection. Upon injection into an organ, chilled collagen gels can thermogel as they reach body temperature or about 37° C.

In some embodiments, the compositions can form a localized mass with prolonged retention by including phase-changing agents and thixotropic agents during preparation.

In some embodiments, the injectable composition is delivered to the cardiac tissue to be treated with needle injection or with a catheter, and the delivery is optionally monitored by ways such as endoscope or fluoroscopy.

In addition to the selection of the components used to make the composition comprising a modified placental tissue, the size of the micronized particles present in the grafts can also vary depending upon their application. In certain aspects, micronized particles having a larger particle size can be used in several applications. For example, the micronized particles (e.g., micronized amnion/chorion tissue graft) having a particle size from 150 μm to 350 μm can be effective in wound healing where it is desirable to reduce or prevent scar formation and enhance soft tissue healing.

In some embodiments, the composition comprises modified placental tissue comprising structural collagens and ECM proteins, regenerative molecules and/or growth factors. In some embodiments, the composition comprises a sufficient amount of growth factors. In some embodiments, the placental growth factors are extracted from modified placental tissue in sufficient quantities so as to provide for an aqueous composition comprising growth factors optionally without the need to form a suspension with modified placental tissue particles. In another embodiment, the composition is free of stem cells or stem cell recruitment factors. Such compositions can also be formulated so as to form localized mass with prolonged retention in vivo.

In some embodiments, the composition comprises modified placental tissue comprising one or more of platelet derived growth factor AA (PDGF-AA), platelet derived growth factor BB (PDGF-BB), granulocyte colony-stimulating factor (GCSF), TGFα, TGFβ, bFGF, EGF, vascular endothelial growth factor (VEGF), keratinocyte growth factor (KGF), hepatocyte growth factor (HGF), nerve growth factor (NGF), heparin binding epidermal growth factor (HB-EGF), angiogenin, angiopoietin-2 (ANG-2), leptin, IL-10, IL-4, placental growth factor (PlGF), TIMP-1, TIMP-2, and TIMP-4. An example of the composition, EpiFix®, has been shown to stimulate cell migration/proliferation (through a multitude of growth factors), reduce scar tissue (via TIMPs), and inhibit inflammation (through IL-10 and IL-4). It is contemplated that the composition can serve as a bandage for the infarct zone. More specifically, the placental tissue material functions as a molecular and mechanical bandage, serving as chemoattractant for endogenous stem cells (e.g., cardiac and/or bone marrow) to migrate to the site of injury and stimulating their proliferation to promote healing, therefore, reduce scar tissue formation and inhibiting inflammation. The composition is biodegradable and therefore is non-inflammatory and nontoxic.

In some embodiments, the composition recruits endogenous stem cells and promote MI healing when used alone. In some embodiments, the composition enhances cell survival and improve the efficacy of bone marrow stem cells when used together with these cells. In some embodiments, the composition is useful in the treatment of MI.

In another aspect, the composition comprising a modified placental tissue described herein are implanted proximal or internal to a diseased and/or injured cardiac tissue in an amount sufficient to attract stem cells and promote endogenous healing. In various aspects, in order to attract stem cells to a damaged cardiac tissue, a sufficient amount of placental tissue is required before the stem cells migrate to the target cardiac tissue. For example, as described in Example 3, stem cells migration occurred in response to EpiFix® in a concentration-dependant manner. A 1.5 mm diameter disk of EpiFix® modified placental tissue was found not to result in a significant migration of stem cells in vitro. However, 4 mm diameter EpiFix® modified placental tissue disks and 12×13 mm square EpiFix® patches show a statistically significant increase in migration of stem cells compared with control cells. One square centimeter of EpiFix® weighs 4 mg. Surprisingly, stem cell migration even in vitro requires a minimum mass of modified placental tissue to induce migration, i.e. more than the mass of a 1.5 mm disk of EpiFix® modified placental tissue. Stated another way, the presence of a sufficient amount of modified placental tissue correlates to a sufficient concentration of stem cell recruiting factors such that stem cell recruitment is achieved. It is contemplated that higher amounts or concentrations of stem cell recruiting factors (such as by using an extract comprising stem cell recruiting factors or addition of stem cell recruiting factors to the modified placental tissue) will facilitate stem cell recruitment.

In addition, Example 4 describes in vivo implantation of a 5×5 mm square EpiFix® modified placental tissue patch, leading to a statistically significant increase in stem cell recruitment in mice, starting at about 2 weeks post-implantation. In this regard, it is contemplated that the use of a larger amount of EpiFix® modified placental tissue would further enhance stem cell recruitment either in a reduced time frame to achieve stem cell recruitment and/or increase the number of stem cells recruited over a given period of time. In various embodiments, the enhancement of stem cell recruitment is at least 5%, 10%, 20%, 30%, 40%, 50%, 60%, 70%, 90%, 100% or more, when compared to the subject not receiving a modified placental tissue graft. Regardless, in at least this example, the data shows that more than a minimal amount of EpiFix® modified placental tissue is required in order to effect stem cell recruitment.

It will be appreciated that the actual amounts of placental tissue or placental tissue extract administered in a specified case will vary according to the specific cardiac tissue to be treated, the particular compositions formulated, the mode of application, and the degree of disease or injury in particular subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999)).

In some aspects, one or more stem cell recruiting factors that enhance stem cell chemotaxis and/or recruitment may be added to the modified placental tissue of the present technology. In other aspects, stem cell recruiting factors can be added to micronized placental tissue. Alternatively, stem cell recruiting factors may be added to layers of a laminate tissue graft. Thus, for example, cytokines, chemokines, growth factors, extracellular matrix components and other bioactive materials can be added to the modified placental tissue to enhance native stem cell recruitment.

Specific non-limiting examples of stem cell recruiting factors may include one or more of the following: CC chemokines, CXC chemokines, C chemokines, or $CX_3C$ chemokines. Other stem cell recruiting factors may further include growth factors such as cc-fibroblast growth factor (αFGF or αFGF-1), β-fibroblast growth factor (βFGF-1 or (βFGF-2), platelet-derived growth factor (PDGF), vascular endothelial growth factor (VEGF-A, B, C, D or E), angiopoietin-1 and -2, insulin-like growth factor (IGF-1), bone morphogenic protein (BMP-2 and -7), transforming growth factor-α and -β (TGF-α and TGF-β), epidermal growth factor (EGF), connective tissue growth factor (CTGF), hepatocyte growth factor (HGF), human growth hormone (HGH), keratinocyte growth factor (KGF), tumor necrosis factor-α (TNF-α), leukemia inhibitory factor (LIF), nerve growth factor (NGF), stromal cell derived factor 1 (SDF-1α), granulocyte macrophage colony stimulating factor (GM-CSF) and other factors as is known in the art.

In another aspect, the modified placental tissue is used in conjunction with conventional treatments, including, but not limited to, coronary bypass procedures, and may also be used in combination with matrices or scaffolds comprised of biocompatible materials, such as collagen, hyaluronic acid, gelatin or combinations thereof.

EXAMPLES

The following examples are put forth so as to provide those of ordinary skill in the art with a complete disclosure and description of how compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Micronized Placental Tissue

Amnion/chorion tissue grafts used here to produce the micronized particles were produced by the process described in US 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryo-block, and the Cryo-block was placed in a Cryo-rack. The Cryo-rack was placed into a liquid nitrogen holding-Dewar flask. Tissue samples were subjected to vapor phase cooling for no more than 30-60 minutes. The Cryo-rack was removed from the Dewar flask, and the Cryo-block was removed from the Cryo-rack. The Cryo-block was placed into the Grinder (SPEX Sample Prep GenoGrinder 2010) and set at 1,500 rpm for 20 minutes. After 20 minutes had elapsed, the tissue was inspected to ensure micronization. If necessary, the tissue was placed back into the Dewar flask for an additional 30-60 minutes, and moved to the grinder for an additional 20 minutes to ensure sufficient micronization. Once the tissue was sufficiently micronized it was sorted using a series of American Standard ASTM sieves. The sieves were placed in the following order: 355 μm, 300 μm, 250 μm, 150 μm, and 125 μm. The micronized material was transferred from the 50 mL vials to the 355 μm sieve. Each sieve was agitated individually in order to thoroughly separate the micronized particles. Once the micronized particles were effectively separated using the sieves, the micronized particles having particle sizes of 355 μm, 300 μm, 250 μm, 150 μm, and 125 μm were collected in separate vials.

Example 2

Preparation of Tissue Grafts with Micronized Placental Tissue

Various modifications and variations can be made to the modified placental tissue, compositions and methods described herein. Other aspects of the modified placental tissue, compositions and methods described herein will be apparent from consideration of the specification and practice of the modified placental tissue, compositions and methods disclosed herein. It is intended that the specification and examples be considered as exemplary.

A detailed description of suitable cross-linking agents and procedures is provided in concurrently filed U.S. Patent Application Ser. No. 61/683,697, filed on Aug. 15, 2012 and entitled PLACENTAL TISSUE GRAFTS MODIFIED WITH A CROSS-LINKING AGENT AND METHODS OF MAKING AND USING THE SAME which application is incorporated herein by reference in its entirety.

A detailed description of reinforced placental tissue grafts is provided in concurrently filed U.S. Patent Application Ser. No. 61/683,699 filed on Aug. 15, 2012 and entitled REINFORCED PLACENTAL TISSUE GRAFTS AND METHODS OF MAKING AND USING THE SAME which application is incorporated herein by reference in its entirety.

A detailed description of making and using micronized placental tissue and extracts thereof is provided in concurrently filed U.S. Patent Application Ser. No. 61/683,700 filed on Aug. 15, 2012 and entitled MICRONIZED PLACENTAL TISSUE COMPOSITIONS AND METHODS OF MAKING AND USING THE SAME which application is incorporated herein by reference in its entirety.

Example 3

Cell Migration in the Presence of EpiFix®

Human mesenchymal stem cells (human MSC) were evaluated in cell culture in the presence of samples of EpiFix® to determine whether the EpiFix® would induce migration of the human MSC. EpiFix® is a layer of amnion and chorion with the epithelial layer intact.

Materials and Methods

Standard migration assays were performed in 24-well cell culture inserts with 8-μm pore membrane filters at the bottom of the insert (see FIG. 1; BD Biosciences). 24 hours prior to the start of the experiment, human MSCs (one donor, passage 3) were cultured in serum free media, and 300 μL of 5 μg/mL fibronectin in PBS was placed into each cell culture insert to enable adsorption of fibronectin to the cell culture insert surface overnight.

Figure 2:
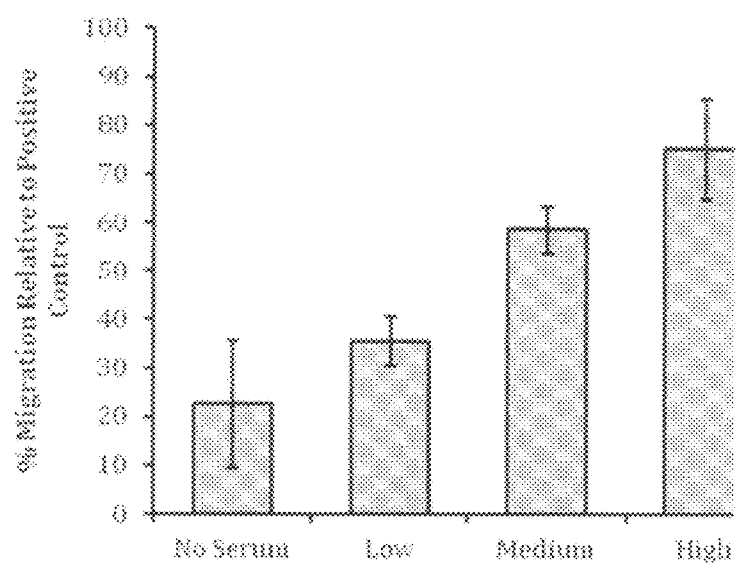
FIG. 2 shows a bar graph of percent cell migration in human mesenchymal stem cells (MSCs) cultured in the presence of various amounts of EpiFix®. Details are described in Example 3.

On the day of the experiment, 700 μL of serum-free culture medium was loaded into the bottom wells of the plate, followed by the addition of differently sized portions of sterilized EpiFix® (Low: 1.5-mm diameter disk; Medium: 4-mm diameter disk; High: 12×13 mm square, trimmed into 3-4 mm square pieces; n=6 EpiFix® tissue donors tested) (FIG. 2). One square centimeter of EpiFix® weighs 4 mg. Serum-free medium and medium with 10% fetal bovine serum (n=6) acted as negative and positive controls, respectively. Human MSCs (40,000 cells in 300 μL) were then loaded into the cell culture inserts and cultured for 24 hours. Then, both sides of the cell culture inserts were rinsed with PBS, and non-migrating cells in the upper portion insert were removed with a cotton-tipped applicator. Cells on the lower side of the insert plus the membrane filter were fixed in 10% formalin for 20 minutes, then rinsed and stained with hematoxylin for 5 min. The number of cells migrating through the membrane were counted on the lower surface of the membrane with an inverted microscope (Nikon TE2000; SPOT Software 4.6).

Data were normalized to the 10% FBS positive control and are expressed as mean±standard deviation of counted, migrated cells per 100× field micrograph for each sample well. Statistical comparisons were performed using a Box-Cox transformation to normalize data variance, followed by one-factor analysis of variance (ANOVA) with Tukey's honestly significant difference post-hoc test.

Results

The Low group (1.5 mm diameter disk) containing the smallest EpiFix® sample was not significantly different from the no serum negative control (see bar graph in FIG. 2). Both the Medium group (4 mm diameter disk) and the High group (12×13 mm square, trimmed into 3-4 mm square pieces) were statistically higher than the no serum control (about 60% and 75% migration relative to control; see FIG. 2), indicating that EpiFix® stimulated cell migration. The High group was not significantly different from the Medium group. The results indicate that the EpiFix® product contains one or more factors that attract human mesenchymal stem cells.

Example 4

Stem Cell Recruitment in Mice Receiving EpiFix® Implants

A study was undertaken to determine whether EpiFix® implanted in normal mice caused recruitment of stem/progenitor cells, focusing on mouse hematopoietic stem cells (HSCs) and mouse mesenchymal stem cells (mouse MSCs).

Materials and Methods

EpiFix® products from six donors were used for implantation in normal mice. A 5×5 mm square of EpiFix® was surgically placed subcutaneously in 4 month old FVB/NJ mice (weighing between about 23.50 g and about 30 g). Four mice were implanted per sample per time point. The time points were 3, 7, 14 and 28 days. The negative controls were normal skin and sham operated mice (surgical incision but no implant). Decellularized dermal matrix (acellular dermal matrix; ADM) was used as the comparative implant (Type I collagen, no cytokines). The implant and overlying skin was harvested for fluorescence-activated cell sorting (FACS).

Implants and overlying skin were harvested, cut into 1 $mm^2$ sections, and incubated in a 0.15% dispase/0.075% collagenase solution at 37° C. for 1 hour. After centrifugation, samples were stained with a lineage antibody cocktail as described below. CD31 antibody was added followed by Alexa Fluor 647 anti-rat secondary antibody. Phycoerythrin-Cy7-conjugated anti-CD45 antibody was incubated last. Samples were prepared and analyzed as described below.

Samples were incubated with a lineage negative ($lin^-$) antibody cocktail (Ter119/CD4/CD8a/Gr-1/CD45R/CD11b) followed by phycoerythrin-Cy5 anti-rat secondary antibody. For mesenchymal stem cell analysis, conjugated antibodies were added against CD45 (phycoerythrin-Cy7) and Sca-1 (fluorescein isothiocyanate). For hematopoietic stem cell analysis, conjugated antibodies were added against CD45 (phycoerythrin-Cy7), c-Kit (phycoerythrin), and Sca-1 (fluorescein isothiocyanate). Samples were incubated with antibodies for 30 minutes and then washed by adding 5 volumes of 2% fetal bovine serum in phosphate-buffered saline with 2 mM ethylenediaminetetraacetic acid. Cells were centrifuged and then re-suspended in propidium iodide for 1 minute at 4° C. Samples were analyzed using an LSR Flow Cytometer. Using CellQuest software), samples were gated for $lin^-$/Sca-$1^+$/$CD45^-$ to define mesenchymal stem cells and for $lin^-$/Sca-$1^+$/c-$Kit^+$/$CD45^+$ to define hematopoietic stem cells.

Results

Figure 3A:
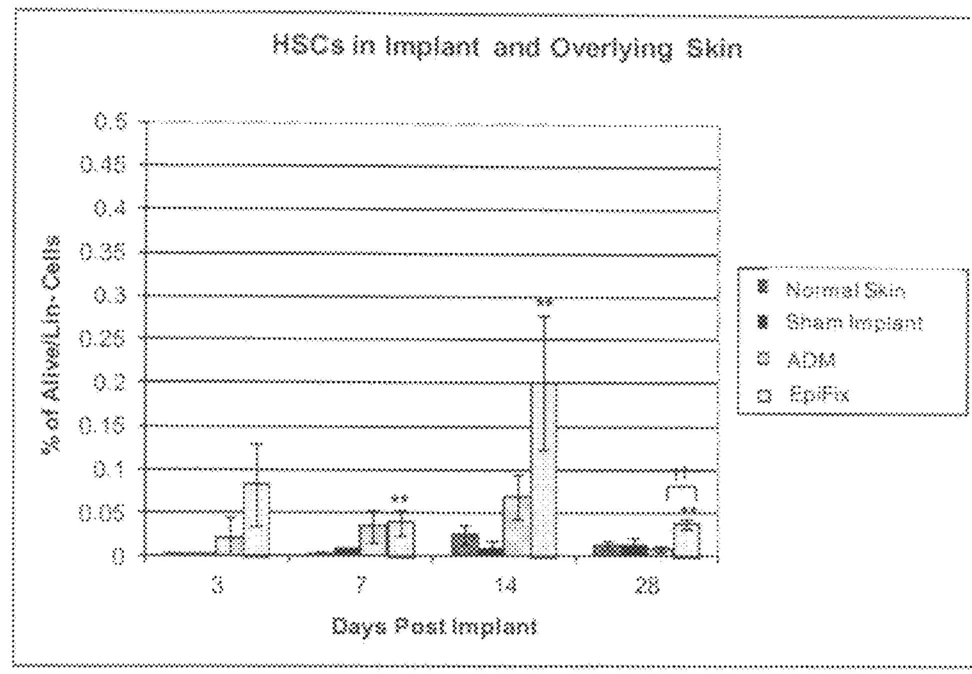
FIG. 3A shows a bar graph of percentage living/$Lin^-$ mouse hematopoietic stem cells in normal skin, sham implant, acellular dermal matrix, and EpiFix® at 3, 7, 14, and 28 days post implant. Values shown are means +/− standard deviation, n=4 specimens.  indicates $p<0.05$ when comparing EpiFix® or control ADM to normal skin and sham implant via one-way ANOVA. †† indicates $p<0.05$ when comparing EpiFix® to control ADM via two tailed t-test.

Mouse HSCs were significantly increased following EpiFix® implantation compared to negative controls at days 7, 14 and 28 (see FIG. 3A). Mouse HSCs remained significantly increased in the EpiFix® samples at day 28 compared to ADM.

Figure 3B:
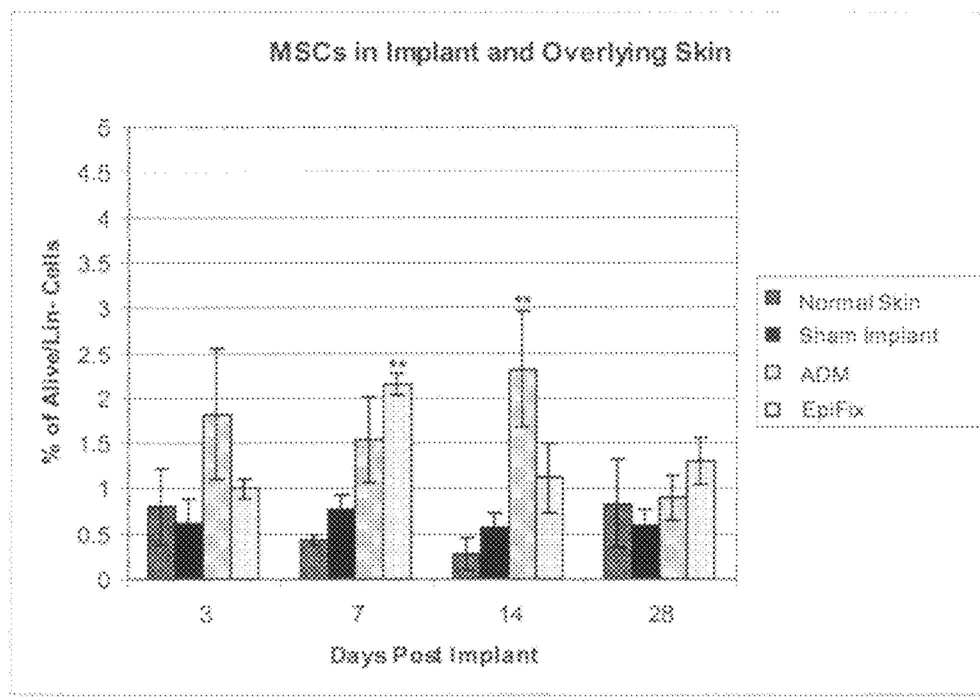
FIG. 3B shows a bar graph of percentage living/Lin mouse mesenchymal cells in normal skin, sham implant, acellular dermal matrix, and EpiFix® at 3, 7, 14, and 28 days post implant. Values shown are means +/− standard deviations, n=4 specimens.  indicates $p<0.05$ when comparing EpiFix® or control ADM to normal skin and sham implant via one-way ANOVA. Details are described in Example 4.

Mouse MSCs were significantly increased following EpiFix® implantation compared to negative controls at day 7 (see FIG. 3B). The average percentages of mouse MSCs were increased at all time points compared to negative controls.

Thus the data described above show that EpiFix® implants effectively recruit both HSCs and MSCs in vivo in normal mice. The data also show that EpiFix® leads to longer term HSC recruitment than acellular dermal matrix (ADM), supporting the hypothesis of a cytokine mediated effect of EpiFix®.

Example 5

Stem Cell Characterization in Mice Receiving EpiFix® Implants

A study was undertaken to characterize stem cells recruited to EpiFix® implantation sites in mice, using flow cytometry and immunohistochemistry.

Materials and Methods

Sterile, Purion® processed EpiFix® (obtained from MiMedx) in a 5×5 mm square patch was implanted subcutaneously through a skin incision on the backs of sixteen 4 month old FVB/NJ mice. Identical skin incisions were made in another sixteen mice to function as a control treatment (sham). For comparison with a collagen scaffold, a 5×5 mm square patch of decellularized human dermis (acellular dermal matrix; ADM) was implanted subcutaneously on the backs of sixteen mice. Un-operated mice were used as a source of "normal" back skin for the analyses.

The surgical site was removed at 3, 7, 14 and 28 days following implantation for analyses of stem cells. Four animals/group were used at each time point. Stem cells were identified with two distinct methods: Fluorescence-activated cell sorting (FACS) and immunohistochemistry (IHC). For the FACS analysis, all cells were isolated from the amnion and associated regenerated tissue. The cells were fluorescently labeled with antibodies to specific stem cell markers. The identity and number of each cell type were determined with a flow cytometer.

For the immunohistochemical analyses, the membrane and associated regenerated tissue was fixed, sectioned for slides, and stained with specific antibodies to stem cells. Two antibodies were used for the immunohistochemistry: anti-CD34, which specifically detects hematopoietic progenitor cells (HPC), and reacts with dermal progenitor cells, endothelial cells, dendritic cells; and anti-CD31, which detects endothelial cells. The stained tissue sections were examined microscopically and the presence and number of specific stem cell types were measured. For the experimental analysis, the relative number of each cell type was counted. The results were calculated as the percentage of each cell type (no. of immunostained cells/total number of cells). Two areas were analyzed immunohistochemically for cell recruitment: the tissue surrounding the implant and the implant itself.

Results

Hematopoietic progenitor cell (HPC) levels were significantly elevated in tissue surrounding EpiFix® implants at days 14 and 28 compared to negative controls. Hematopoietic progenitor cells were significantly increased in the tissue surrounding the EpiFix® implant at days 14 and 28 compared to collagen scaffold ADM control.

Progenitor cells were recruited into the EpiFix® implant. Intra-implant hematopoietic progenitor cells peaked at day 14 in the EpiFix® implant, and remained elevated at day 28. Average intra-implant hematopoietic progenitor cells were increased in the EpiFix® implant at days 14 and 28 compared to control ADM. Progenitor cells were not recruited into the ADM control implant.

Vascularization of the EpiFix® implant steadily increased from day 14 to day 28. The amount of new vessel formation in the EpiFix® implant was significantly greater than that in the ADM control on day 28.

These data establish that EpiFix® contains one or more factors that recruit both hematopoietic stem cells and mesenchymal stem cells to the site of injury. More of these stem cells were found in the EpiFix® membrane and associated regenerated tissue than in the sham. EpiFix® was significantly more effective than the control decellularized collagen scaffold in recruiting progenitor cells to colonize the implant site. There were more progenitor cells in the EpiFix® membrane than in the control collagen scaffold.

EpiFix® also induced new blood vessel formation in the associated regenerated tissue and the EpiFix® membrane itself. Vascularization in the EpiFix® membrane was significantly higher than in the collagen scaffold control.

Example 6

Effects of AmnioFix® and EpiFix® on Cardiac Repair

A study was undertaken to study the effects of AmnioFix® and EpiFix® membranes on cardiac repair after acute myocardial infarction (MI), including infarct size and cardiac remodeling. Both AmnioFix® and EpiFix® (obtained from MiMedx) are derived from the amniotic membrane and contain structural collagens and extracellular matrix proteins, as well as a number of growth factors and cytokines, including PDGF-AA, PDGF-BB, TGFα, TGFβ, bFGF, EGF, VEGF, IL-10, IL-4, PlGF, TIMP-1, TIMP-2, AND TIMP-4.

Materials and Methods

The experiment was performed using immune-compromised NOD/SCID mice in an effort to eliminate any potential engagement of the immune systems in response to the xenograft AmnioFix® or EpiFix® membrane. The wild-type mice was used for comparison.

The left descending coronary artery (LAD) of the NOD/SCID or wild-type mice was ligated to induce MI. The MI mice were either treated with the AmnioFix membrane®, EpiFix® membrane or saline as a control. Eight weeks post treatment, the mice were analyzed for infarct size, cardiac remodeling, cell apoptosis and proliferation as well as stem cell mobilization.

Results

Figure 4A:
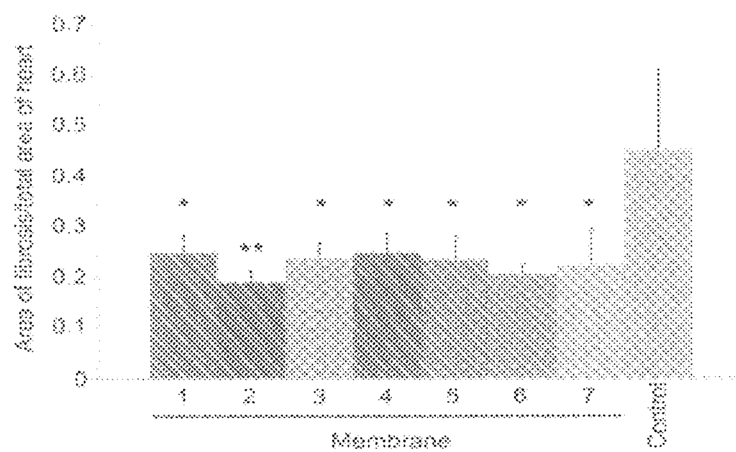
FIGS. 4A and 4B demonstrate that AmnioFix® and EpiFix® membrane protected mice from damage following experimentally induced myocardial infarction (MI). Treatment of mice with either the AmnioFix® or EpiFix® membranes significantly reduced infarct size on NOD/SCID and wild-type mice following MI. Similar levels of protection were seen for each membrane type.
Figure 4B:
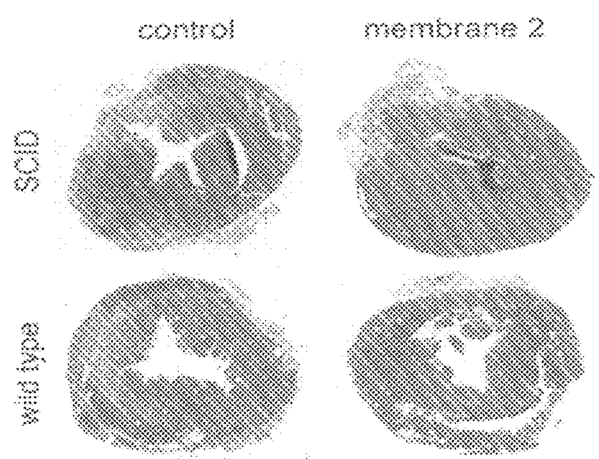

Both the AmnioFix® and the EpiFix® membrane treated mice showed decreased infarct area following coronary artery ligation compared to control (saline) treated mice (FIGS. 4A and 4B). There was no statistically significant difference between the EpiFix® and AmnioFix®-treated mice in infarct size. Several mice did not recover from the coronary artery ligation but this was due to surgical mortality, rather than the post-surgical membrane treatment.

Figure 5A:
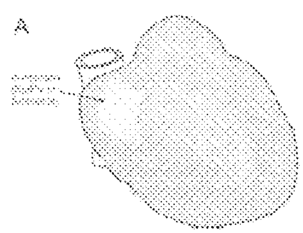
FIGS. 5A-5C demonstrate that treatment with the AmnioFix® and EpiFix® membrane increased the number of c-kit+ cells.
Figure 5B:
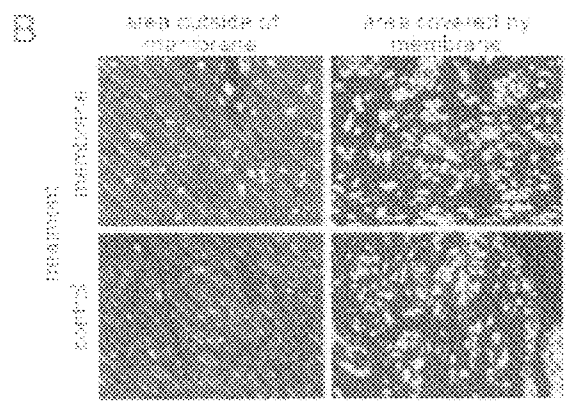
Figure 5C:
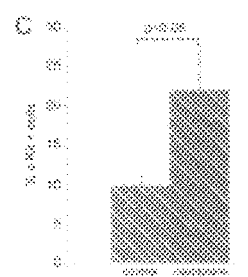

To determine if the decreased infarct size was due to recruitment of c-kit positive stem cells from the bone marrow or locally from the heart, sections of the cardiac tissue were stained for c-kit and analyzed. There was a significant increase in c-kit positive stem cells both in the region directly in contact with the membrane, as well as regions of the heart peripheral to the membrane (FIGS. 5A-5C). This indicates that cardiac repair present outside of the region that had direct contact with the membrane (either the AmnioFix® or EpiFix® membrane) may be mediated by stem cells. This may contribute to the observed overall decrease in the fibrous area of the heart.

Figure 6A:
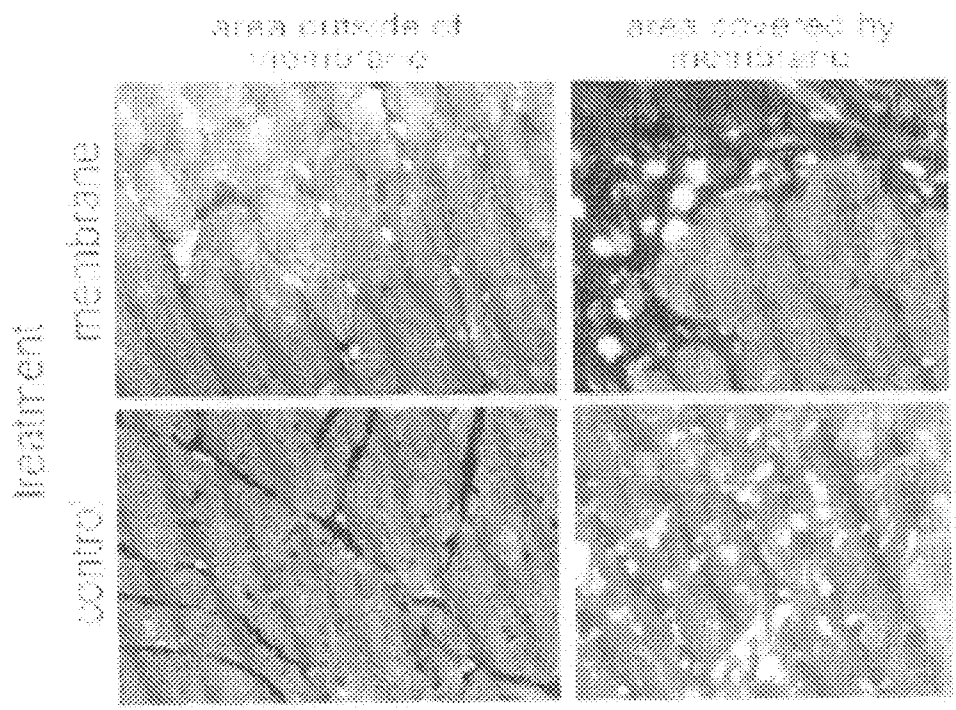
FIGS. 6A and 6B demonstrate that Ki67 levels were elevated in membrane-treated heart tissue both in the area covered by the membrane and outside of the membrane-treated area.
Figure 6B:
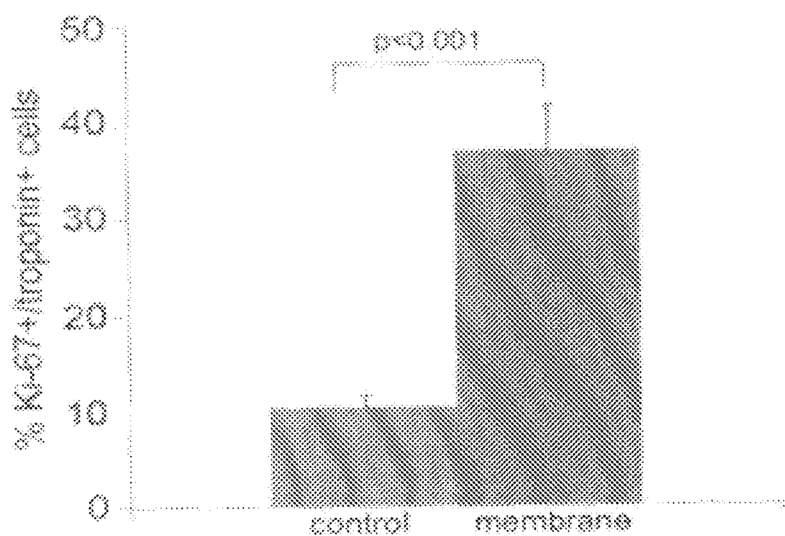

Furthermore, there was a significant increase in the level of the cell proliferation marker Ki-67 in the membrane-treated hearts compared to the control group (FIGS. 6A and 6B). The Ki-67 expression extended beyond the region with direct contact with the membrane into the distal heart tissue. This further supports the paracrine effects of the amniotic membrane products in stimulating cell proliferation and tissue repair.

Figure 7A:
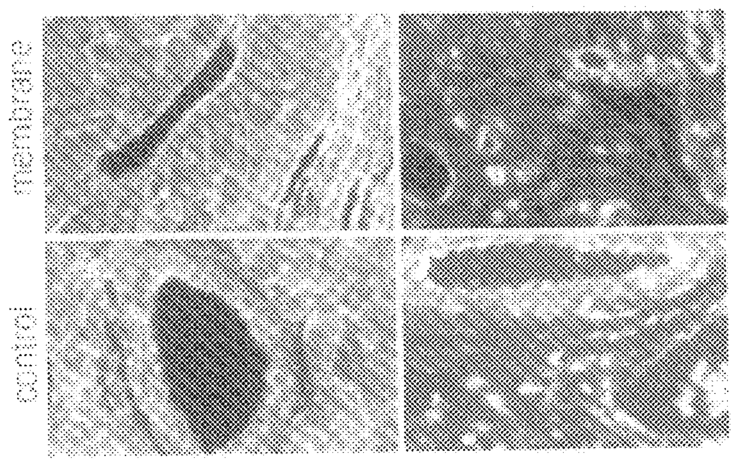
FIGS. 7A and 7B demonstrate that the membrane-treated hearts had significantly increased numbers of blood vessels compared to control-treated tissue.
Figure 7B:
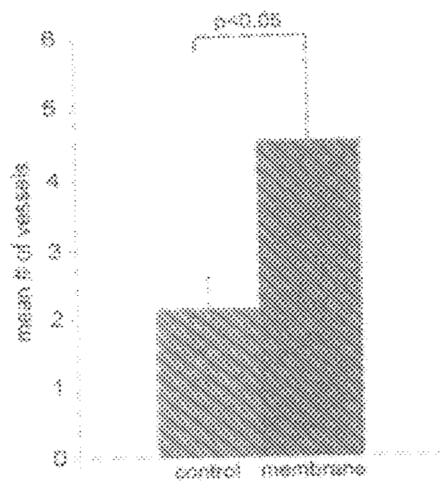

In addition, there was an increase in the number of blood vessels found in the membrane-treated hearts as indicated by CD31 staining compared to the control treated mice (FIGS. 7A and 7B). This indicates that the membrane treatment increased angiogenesis, resulting in improved blood supply, promoting cardiac repair.

Figure 8A:
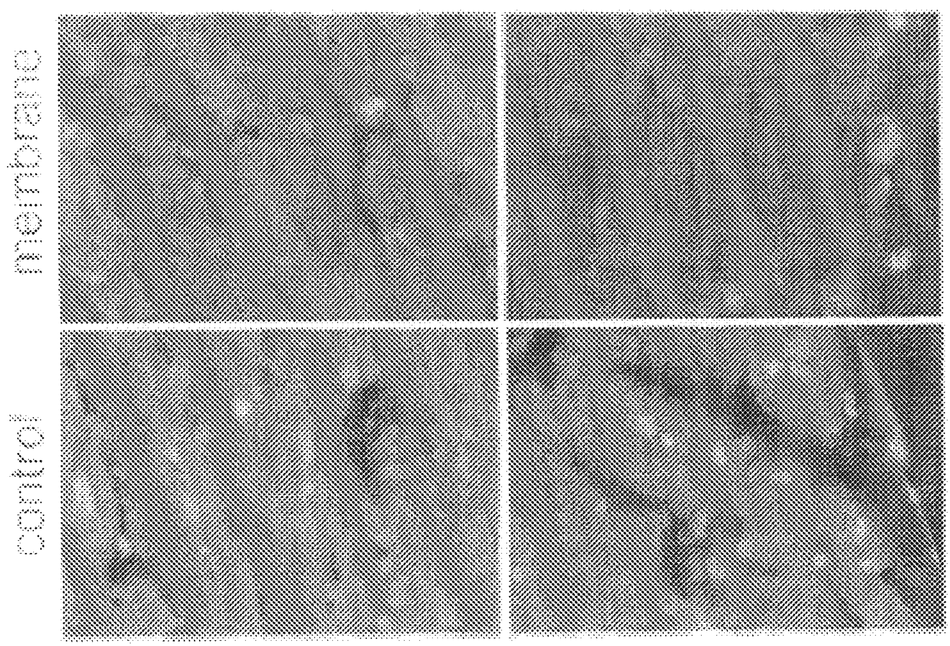
FIGS. 8A and 8B demonstrate that membrane treatment significantly decreased apoptosis following MI.
Figure 8B:
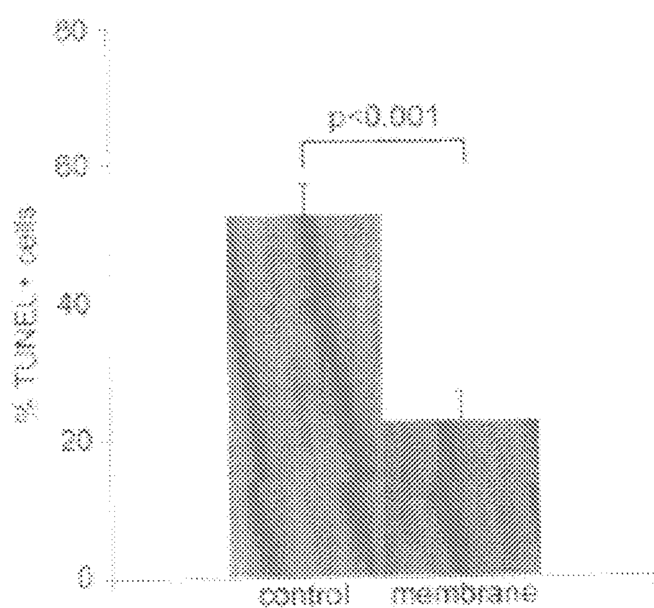

Conversely, there was a significant decrease in apoptosis in the membrane treated hearts compared to the saline treatment as measured by TUNEL staining (FIGS. 8A and 8B). These data indicate that AmnioFix® and EpiFix® inhibit cell apoptosis and promote cell survival, perhaps through improved blood supply and other paracrine mechanisms.

In summary, Example 6 demonstrates that the treatment with either EpiFix® or AmnioFix® membranes protected the mouse hearts following coronary artery ligation-induced MI. Each of these membranes reduced the infarct area to similar extents. This decrease in infarct size was seen irrespective of the type of mice treated (NOD/SCID vs. wild-type mice). The pro-repair effects were associated with elevated levels of c-Kit+ stem cells, increased cell proliferation and decreased cell apoptosis. In addition, there was an increase in the mean numbers of vessels in the treated hearts. These results show that treatment with EpiFix® or AmnioFix® improve cardiac repair following MI through multiple paracrine effects. There is no significant difference in the efficacy of the EpiFix® compared to the AmnioFix® in these experiments.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for treating a cardiac condition in a patient in need thereof, comprising administering to said patient a sufficient amount of a composition comprising a modified placental tissue or an extract of a placental tissue to an area proximate to the heart of the patient, wherein the amount of said modified placental tissue or extract is sufficient to promote stem cell recruitment to said area;

wherein the modified placental tissue comprises an amnion having an epithelial cell layer and/or a fibroblast cell layer; wherein the composition is micronized.

2. The method of claim 1, wherein said cardiac condition is an inflammatory heart condition, which method comprises placing an effective amount of said composition at or adjacent to an inflammatory cardiac tissue without obstructing the function thereof, wherein the modified placenta tissue or extract is placed under conditions that promote treatment of the inflammation in said cardiac tissue.

3. The method of claim 1, wherein the cardiac condition is selected from the group consisting of acute myocardial infarction, myocardial infarction, cardiomyopathy, unstable angina, refractory angina, heart attack, heart failure, cor pulmonale, vein graft diseases, coronary heart diseases, occlusive coronary thrombus, valvular heart diseases, inflammatory cardiomegaly, atherosclerosis, acute pericarditis, Dressler syndrome, an inflammatory heart condition and a necrotizing heart condition.

4. The method of claim 1, wherein the composition comprises an effective amount of stem cell recruiting factors.

5. The method of claim 1, wherein the composition comprises an effective amount of growth factors.

6. The method of claim 1, wherein the composition comprises an effective amount of angiogenesis inducing factors.

7. The method of claim 1, wherein the composition comprises one or more of PDGF-AA, PDGF-BB, TGFa, TGFβ, bFGF, EGF, VEGF, IL-10, IL-4, P1GF, TIMP-2, and TIMP-4.

8. The method of claim 7, wherein stem cells are recruited by the composition.

9. The method of claim 1, wherein the placental tissue has a mass sufficient to recruit stem cells to an area to be treated.

10. The method of claim 1, wherein the cardiac condition is a necrotizing heart condition.

11. The method of claim 1, wherein the cardiac condition is selected from the group consisting of heart failure, cor pulmonale, vein graft diseases, coronary heart diseases, occlusive coronary thrombus, valvular heart diseases, inflammatory cardiomegaly, atherosclerosis, inflammation of a heart valve, inflammatory cardiomyopathy, myocarditis, endocarditis, a necrotizing condition, chronic pericarditis, acute pericarditis and Dressler syndrome.

12. The method of claim 1, wherein the composition is in an injectable form.

13. The method of claim 1, wherein the composition is a patch.

14. The method of claim 1, wherein the composition is in sustained or continuous release form.

15. The method of claim 1, wherein the composition comprises a modified placental tissue.

16. The method of claim 1, wherein the composition comprises an extract of a placental tissue.

* * * * *